US00PP20863P2

(12) United States Plant Patent
Bradford

(10) Patent No.: US PP20,863 P2
(45) Date of Patent: Mar. 23, 2010

(54) INTERSPECIFIC TREE NAMED 'BLACKRED VIII'

(50) Latin Name: ***Prunus* sp.**
Varietal Denomination: Blackred VIII

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/316,597

(22) Filed: Dec. 15, 2008

(51) Int. Cl.
*A01H 5/00* (2006.01)

(52) U.S. Cl. ..... Plt./180

(58) Field of Classification Search ..... Plt./180, Plt./184, 186
See application file for complete search history.

(56) References Cited

U.S. PATENT DOCUMENTS

PP16,369 P2 3/2006 Bradford

*Primary Examiner*—June Hwu

(57) ABSTRACT

The present invention relates to an interspecific tree and more particularly to a medium size, moderately vigorous, hardy, and very productive tree. Being self-unfruitful, the present variety requires cross pollination from an apricot, interspecific, or plum that blooms during the early season. The present variety's abundance of blossoms and moderate pollen production entices strong bee activity to facilitate pollination. The fruit matures under the ecological conditions described during the latter part of August, with first picking on Aug. 23, 2008. The fruit is uniformly large in size, blackish red in skin color, clingstone in type, oblate in shape, mostly red to orange in flesh color, firm in texture, and outstanding in flavor.

1 Drawing Sheet

Botanical classification: *Prunus* sp.
Varietal denomination: 'BLACKRED VIII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'BLACKRED VIII.'

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one such house containing an unpatented red plum, code named 19P442, was crossed by me in this manner. To pollinate this red plum, I selected bouquets from several sources of apricot and interspecific plum-apricot hybrid trees without keeping specific written details. Upon reaching maturity the fruit from this red plum tree was harvested and the seeds were removed, cracked, stratified and germinated as a group with the label "H8A". They were grown as seedlings on their own root in my greenhouse and upon reaching dormancy transplanted to a cultivated area of my experimental orchard located near Le Grand, Calif. in Merced County (San Joaquin Valley). During the summer of 2004 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was true to type.

The present variety is similar to its seed parent, '19P442', by producing an abundant amount of fruit that is firm in texture and red in flesh color, but is distinguished therefrom by producing fruit that is sweeter in flavor, that is much larger in size, and that matures about two months later.

The present variety is similar to 'Plumsweet V' (U.S. Plant Pat. No. 16,369) interspecific tree by being self-unfruitful and by producing fruit that is clingstone in type, that is mostly dark purple to black in skin color, that has a significant degree of red in the flesh color, that is very sweet in flavor, and that matures in the latter part of August, but is distinguished therefrom by blooming earlier and by producing fruit that is much larger in size, more oblate in shape, less juicy, and much less prone to shoulder wrinkling after harvest.

SUMMARY OF VARIETY

The present interspecific variety is characterized by a medium size, moderately vigorous, hardy, and very productive tree. Being self-unfruitful, the present variety requires cross pollination from an apricot, interspecific, or plum that blooms during the early season. The present variety's abundance of blossoms and moderate pollen production entices strong bee activity to facilitate pollination. The fruit matures under the ecological conditions described during the latter part of August, with first picking on Aug. 23, 2008. The fruit is uniformly large in size, blackish red in skin color, clingstone in type, oblate in shape, mostly red to orange in flesh color, firm in texture, and outstanding in flavor.

DRAWING

The accompanying photograph consists of four whole fruits positioned to display the characteristics of the skin color and form, one fruit divided transversely to the suture plane to reveal the flesh and stone, typical leaves, and three insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Sep. 3, 2008, on the original tree during its seventh growing season. The flower and bud descriptions were developed during the previous blooming season. All major color code designations are by reference to the Inter-Society Color Council, National Bureau of Standards. Common color names are also used occasionally.

Parentage

Seed parent: 19P442 plum (unpatented).
Pollen parent: Unknown.

Tree

Size: Medium, reaching a height of 12' [3.66 m.] and a spread of 7' [2.13 m.] after seven growing seasons utilizing typical dormant pruning.

Vigor: Moderately vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Perpendicular V form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable early seasonal blooming apricot, interspecific, or plum, such as 'Blackred II' (U.S. Plant patent application Ser. No. 11984889 filed on Nov. 26, 2007).

Bearing: Regular bearer, with no crop failures observed.

Trunk:

- *Size.*—Medium, reaching a maximum diameter of 3¾" [95.3 mm.] after the seventh growing season.
- *Texture.*—Medium shaggy.
- *Bark color.*—A Dark grayish brown [62. d.gy.Br] and Grayish brown [61. gy.Br] variegation with Light yellowish brown [76. l.yBr] crevices present.
- *Lenticels.*—Approximate Number Per Square Inch: 8. Color: Light brown [57. l.Br]. Average Size: ⅜" [9.5 mm.]. Shape: Elongated, eye-shaped.

Branches:

- *Size.*—Diameter of limb is 2¼" [57.2 mm.] measured 12" above the crotch, 1½" [38.1 mm.] measured 12" above second fork.
- *Texture.*—Smooth on first year wood, increasing roughness with age.
- *Color.*—1st Year Wood Topside: Deep brown [56. deep Br]. 1st Year Wood Underside: Brilliant yellow green [116. brill.YG]. 2nd Year Wood: Strong brown [55. s.Br]. Older Wood: A Dark grayish brown [62. d.gy.Br] and Deep brown [56. deep Br] variegation with Light orange yellow [70. l.OY] crevices present.
- *Lenticels.*—Number Per Square Inch: More than 60 on second year wood. Color: Brownish orange [54. brO]. Average Size: 1/64" [0.4 mm.]. Shape: Elongated, eye-shaped.

Leaves:

- *Size.*—Medium. Average Length: 4" [101.6 mm.]. Average Width: 1 15/16" [49.2 mm.].
- *Arrangement.*—Alternate.
- *Thickness.*—Medium.
- *Form.*—Elliptical.
- *Apex.*—Acuminate.
- *Base.*—Acute with an average angle base angle of 75 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: 9/16" [14.3 mm.]. Average Thickness: 1/16" [1.6 mm.]. Color: Pale yellow green [121. p.YG], often Grayish red [19. gy.R] where exposed to direct sunlight.
- *Stipules.*—Number: 2 per leaf at the young stage, up to 6 per growing tip. Average Length: ⅜" [9.5 mm.]. Color: Light yellow green [119. l.YG] becoming Light reddish brown [42. l.rBr] with age.
- *Glands.*—Number: Mostly 2 per leaf. Position: Alternately and oppositely positioned at the intersection of the petiole and the leaf blade. Size: Small. Form: Globose. Color: Light yellow green [119. l.YG] becoming Dark yellowish brown [78. d.yBr] with age. Leaf buds: Pointed, medium.

Flower buds:

- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Tip color.*—White [263. White].

Flowers: Perfect, complete, perigynous, usually a single pistil, typically thirty or more stamens, five sepals and petal locations alternately positioned.

- *Average flower diameter.*—1" [25.4 mm.].
- *Number of petals.*—Five, no double blossoms observed.
- *Petal shape.*—Oval to circular.
- *Petal margin.*—Entire, smooth to slightly wavy.
- *Average petal diameter.*—½" [12.7 mm.].
- *Average petal length.*—9/16" [14.3 mm.].
- *Petal apex.*—Rounded.
- *Petal base.*—Obtuse.
- *Petal color.*—White [263. White] on both sides.
- *Anther color.*—Light orange yellow [70. l.OY].
- *Stigma color.*—Light greenish yellow [101. l.gY].

*Sepal color.*—Strong yellow green [117. s.YG] on the outer surface with a distinct Grayish red [19. gy.R] tinge on the edges.
*Sepal length.*—5/32" [4.0 mm.].
*Sepal width.*—5/32" [4.0 mm.].
*Sepal apex.*—Rounded to elliptical to match the width and length.
*Sepal margin.*—Fairly smooth, with slight serration toward the apex.
*Average pistil length.*—5/8" [15.9 mm.].
*Average stamen length.*—1/2" [12.7 mm.].
*Fragrance.*—Moderate.
*Pollen production.*—Moderate.
*Blooming period.*—Early, with 'Ambra' plum (unpatented).
*Bloom density.*—Heavy.
*Number per cluster.*—2 to 8, average 3.

*Onset of bloom.*—One percent on Feb. 22, 2008.
*Date of full bloom.*—Mar. 2, 2008.
*Duration of bloom.*—One to two weeks, dependent on ambient temperature.

FRUIT

Maturity when described: Firm ripe, Sep. 3, 2008.
Date of first picking: Aug. 23, 2008.
Date of last picking: Sep. 8, 2008.
Size: Uniform, large.
*Average diameter axially.*—2 7/16" [62 mm.].
*Average diameter across cheek plane.*—2 7/8" [73 mm.].
*Average diameter across suture plane.*—2 3/4" [70 mm.].
*Typical weight.*—6.8 ounces [193 grams].
Form: Uniformly oblate, symmetrical.
*Longitudinal section form.*—Oblate.
*Transverse section through diameter.*—Round.
Suture: An inconspicuous line located in a very shallow groove extending from the base to the pistil point.
Ventral surface: Rounded, lightly lipped throughout.
Lips: Equal.
Cavity: Flaring, circular, suture showing on one side, stem markings rarely occurring.
*Depth.*—7/16" [11.1 mm.].
*Breadth.*—1" [25.4 mm.].
Base: Truncate, slightly cordate if viewed parallel to the suture.
Apex: Truncate.
Pistil point: An inconspicuous dot located at the end of the suture.
Stem: Large.
*Average length.*—1/2" [12.7 mm.].
*Average width.*—1/8" [3.2 mm.].
Skin:
*Thickness.*—Medium.
*Surface.*—Smooth.
*Tenacity.*—Tenacious to the flesh.
*Astringency.*—Slight.
*Tendency to crack.*—Rare.
*Color.*—Blackish red [21. blackish R] over a Very deep red [14. v.deep R] background with Light yellowish brown [76. l.yBr] freckling throughout the apex.
*Bloom.*—Abundant.
Flesh:
*Color.*—Pale yellowish pink [31. p.yPk] near the stone bleeding evenly into Strong red [12. s.R] toward the skin with Moderate red [15. m.R] fibers throughout.
*Surface of pit cavity.*—Covered with Moderate yellowish pink [29. m.ypk] broken fibers when twisted away from stone.
*Amygdalin.*—Moderate.
*Juice.*—Moderate, rich.
*Texture.*—Firm, tough, crisp.
*Fibers.*—Abundant, fine, tough.
*Ripens.*—Somewhat earliest at apex.
*Flavor.*—A very sweet blend of mild acid and sugar, typically 20–24 brix.
*Aroma.*—Slight.
*Eating quality.*—Excellent.

STONE

Type: Clingstone.
Form: Oval.
Hilum: Narrow, oblong.
Base: Straight.
Apex: Rounded, with a small 1/32" [0.8 mm.] protruding tip.
Sides: Equal.
Surface: Rough throughout with a shallow groove on each side of the dorsal fin.
External color of stone: Dark orange yellow [72. d.OY] when first removed.
Pit wall color when cracked: Moderate yellowish brown [77. m.yBr].
Cavity surface color: Deep brown [56. deep Br].
Average pit wall thickness: 1/16" [1.6 mm.].
Average width: 5/8" [15.9 mm.].
Average length: 7/8" [22.2 mm.].
Average breadth: 3/8" [9.5 mm.].
Tendency to split: Slight.
Kernel:
*Form.*—Oval.
*Skin color.*—Strong yellowish brown [74. s.yBr] when dry.
*Pellicle color.*—Deep brown [56. deep Br].
*Vein color.*—Deep brown [56. deep Br].
*Taste.*—Bitter.
*Viable.*—Yes.
*Average width.*—7/16" [11.1 mm.].
*Average length.*—9/16" [14.3 mm.].
*Amygdalin.*—Moderate.

Use

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'Plumsweet V' (U.S. Plant Pat. No. 16,369) interspecific tree by being self-unfruitful and by producing fruit that is clingstone in type, that is mostly dark purple to black in skin color, that has a significant degree of red in the flesh color, that is very sweet in flavor, and that matures in the latter part of August, but is distinguished therefrom by blooming earlier and by producing fruit that is much larger in size, more oblate in shape, less juicy, and much less prone to shoulder wrinkling after harvest.

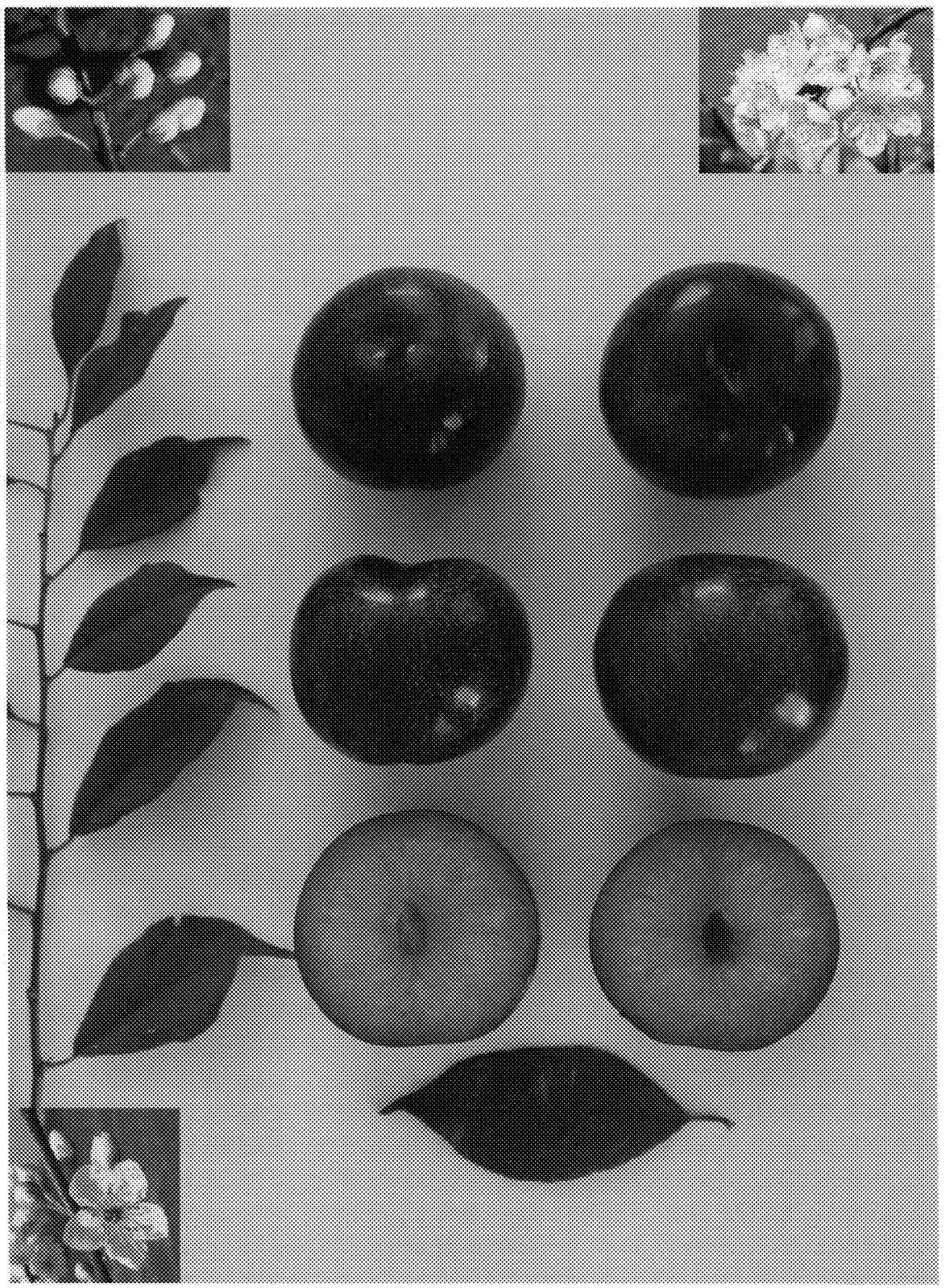

* * * * *